(12) United States Patent
Masson

(10) Patent No.: US 7,597,688 B1
(45) Date of Patent: Oct. 6, 2009

(54) CANNULA APPARATUS WITH INFLATABLE SEAL AND ADJUSTABLE LENGTH

(76) Inventor: Marcos V. Masson, 3834 University Blvd., Houston, TX (US) 77005

( * ) Notice: Subject to any disclaimer, the term of this patent is extended or adjusted under 35 U.S.C. 154(b) by 808 days.

(21) Appl. No.: 11/140,170

(22) Filed: May 31, 2005

Related U.S. Application Data

(63) Continuation-in-part of application No. 11/021,419, filed on Dec. 27, 2004.

(51) Int. Cl.
A61M 1/00 (2006.01)
(52) U.S. Cl. ............. 604/323; 600/154; 604/96.01
(58) Field of Classification Search ............ 452/69; 600/154; 604/96.01, 96.1, 96, 506, 164.11, 604/323
See application file for complete search history.

(56) References Cited

U.S. PATENT DOCUMENTS

| | | | | |
|---|---|---|---|---|
| 4,757,616 A | * | 7/1988 | Hills | ........................ 33/488 |
| 4,973,321 A | * | 11/1990 | Michelson | ................. 604/523 |
| 5,634,937 A | * | 6/1997 | Mollenauer et al. | ........ 606/213 |
| 5,727,770 A | | 3/1998 | Dennis | |
| 5,797,888 A | | 8/1998 | Yoon | |
| 5,989,224 A | | 11/1999 | Exline et al. | |
| 5,993,470 A | * | 11/1999 | Yoon | .......................... 606/185 |
| 5,997,515 A | * | 12/1999 | de la Torre et al. | ......... 604/256 |
| 6,159,182 A | | 12/2000 | Davis et al. | |
| 6,276,661 B1 | * | 8/2001 | Laird | ....................... 251/61.1 |
| 6,439,541 B1 | * | 8/2002 | Nosel et al. | ............. 251/149.1 |
| 6,491,696 B1 | * | 12/2002 | Kunkel | ....................... 606/105 |
| 6,551,282 B1 | | 4/2003 | Exline et al. | |
| 6,673,058 B2 | * | 1/2004 | Snow | ......................... 604/506 |
| 7,153,319 B1 | * | 12/2006 | Haberland et al. | .......... 606/185 |
| 7,322,964 B2 | * | 1/2008 | Pajunk et al. | ............... 604/246 |
| 2001/0029388 A1 | * | 10/2001 | Kieturakis et al. | ......... 606/190 |
| 2002/0189611 A1 | * | 12/2002 | Greenwood et al. | .... 128/200.23 |
| 2003/0229264 A1 | * | 12/2003 | Connors et al. | ............... 600/29 |
| 2004/0111061 A1 | * | 6/2004 | Curran | ....................... 604/174 |
| 2004/0167473 A1 | * | 8/2004 | Moenning | ............. 604/164.02 |
| 2005/0203467 A1 | * | 9/2005 | O'Heeron et al. | ........... 604/249 |
| 2005/0261661 A1 | * | 11/2005 | McFarlane | .................. 604/506 |

* cited by examiner

*Primary Examiner*—Nicholas D Lucchesi
*Assistant Examiner*—Gerald Landry, II
(74) *Attorney, Agent, or Firm*—Egbert Law Offices

(57) ABSTRACT

A cannula has a tubular body, an inflatable ring affixed within the tubular body adjacent proximal end thereof, and a valve connected to a channel extending to the inflatable ring. The valve is suitable for allowing a liquid to be passed into the inflatable ring from a syringe. The inflatable ring is expandable into the longitudinal channel when the liquid is introduced thereinto. The tubular body has an outer sleeve adjustably receiving an inner sleeve at the distal end of the tubular body. Numerical indicia are formed on the inner sleeve.

11 Claims, 5 Drawing Sheets

CANNULA APPARATUS WITH INFLATABLE SEAL AND ADJUSTABLE LENGTH

RELATED U.S. APPLICATIONS

The present application is a continuation-in-part of U.S. patent application Ser. No. 11/021,419, filed on Dec. 27, 2004, and entitled "Cannula having Inflatable Seal", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates generally to cannulae. More particularly, the present invention relates to various liquid-tight seals that are positioned at the proximal end of the cannula. Additionally, the present invention relates to inflatable seals which prevent the release of water through the interior of the cannula during the performance of surgical procedures with an instrument extending through the cannula.

BACKGROUND OF THE INVENTION

Many medical procedures require the use of a cannula, through which one or more medical instruments are inserted into a patient and then removed from the patient. For example, in a variety of laparoscopic medical procedures, a cannula is positioned with its distal end inside the patient and its proximal end outside the patient. One or more medical instruments can be inserted through the cannula into the patient. For example, each of a sequence of instruments (including an endoscope) can be inserted through the cannula into the patient and then withdrawn (in the opposite direction) out from the patient and cannula.

During many such procedures, it is necessary to maintain an insufflated working space within the patient (by maintaining insufflating gas at sufficiently high pressure in the working space) while the distal end of the cannula extends into the working space. For use during these procedures, the cannula must be provide with a seal or seals for preventing undesired fluid escape from within the patient out through the cannula. The term "fluid" is used herein to denote either a gas or a liquid. One such seal will prevent fluid escape from the cannula when no instrument occupies the cannula's channel. A fluid seal is implemented in the form of a flapper valve, a duckbill valve, or other valve, which is biased in a closed position at times when no instrument occupies the cannula's channel to provide a fluid seal preventing fluid flow through the instrument at such times. When the distal end of the instrument is inserted into the channel and the instrument has advanced through the channel toward the patient, the instrument opens the fluid seal.

Typically, an additional seal is employed in a cannula to provide a fluid seal around the instrument's outer periphery and to prevent fluid flow through the space between the instrument and the wall of the channel. Such instrument seals are very important for enhancing the ease with which a medical procedure can be carried out. In many shoulder surgeries, up to twenty gallons of fluid can be used during the surgical procedure. Ultimately, the fluid must escape from the human body in one direction or another. In certain circumstances, when poor seals are used, the water is continually escaping around the periphery of the instrument onto the surgeon, the surgical assistants, the patient and the operating room environment. The rapidly escaping liquid greatly complicates the ability to carry out a simple and safe surgical procedure. In general, all prior art instrument seals have proven to be very ineffective at preventing the liquid escape through the interior of the cannula. As such, a need has developed with which to make an instrument seal which effectively prevents the loss of liquids around the periphery of the instrument during the surgical procedure.

In the past various patents have issued relating to such instrument seals. For example, U.S. Pat. No. 5,727,770, issued on Mar. 17, 1998 to W. G. Dennis, describes a double valve cannula seal for preventing the escape of liquids or gases through the cannula. The seal has a diaphragm valve with a circular aperture to seal the cannula when an instrument is inserted and a spilt conical valve to seal the cannula when no instrument is present. A pair of diametrically opposed ribs are positioned beneath the end member and are aligned with the split in the conical valve so as to abut the open end of the cannula and act as pivot points to impart compressive force against the two halves of the conical valve to improve the effectiveness of the seal.

U.S. Pat. No. 5,797,888, issued on Aug. 25, 1998 to I. Yoon, teaches a cannula with a universal seal. The cannula is an elongate tubular body having a distal end adapted to be disposed within the anatomical cavity and a proximal end adapted to be disposed externally of the anatomical cavity. A seal member is disposed along the tubular body of the cannula. A tubular pusher is disposed in the tubular body and insertable through the seal to move the seal member from a normally closed position preventing fluid flow through the cannula to an open position allowing instruments of various sizes to be introduced through the tubular body via the tubular pusher without contacting the seal.

U.S. Pat. No. 5,989,224, issued on Nov. 23, 1999 to Exline et al., discloses a universal seal for use in endoscopic surgery. A two-part seal housing encloses the universal seal in an annulus surrounding an insertion port. The outer periphery of the universal seal is clamped between the two parts at the outer edge of the annulus. An inner ring of the universal seal is free to move from side-to-side within the annulus while maintaining rubbing contact with the upper and lower surfaces of the annuluses for vertical support. The seal housing and universal seal are mounted on a proximal end of a cannula which allows access therethrough for the endoscopic surgery. U.S. Pat. No. 6,551,282, issued on Apr. 22, 2003 to Exline et al., also teaches similar type of seal for use on a cannula.

U.S. Pat. No. 6,159,182, issued on Dec. 12, 2000 to Davis et al., provides a reusable cannula with a disposable seal. The seal assembly is designed for use with the cannula during a simple medical procedure. The seal includes both a flapper valve fluid seal and at least one instrument seal. The seal assembly has a body and a flange that can be snapped onto the cannula before use and readily removed after use. The flapper valve has a over-centered hinge. The sealing flange seals the cannula when a medical instrument is inserted through the seal assembly even when the sacrificial flange has been cut during insertion of the instrument.

It is an object of the present invention to provide a seal for use in a cannula which prevents liquid escape therethrough.

It is another object of the present invention to provide a cannula seal that can be adapted to various diameters of instruments.

It is a further object of the present invention to provide a seal for use in a cannula which allows full use of the instrument even when the seal is in liquid-tight engagement therewith.

It is still a further object of the present invention to provide a seal for use on a cannula which is easy to use, relatively inexpensive, and easy to manufacture.

It is a further object of the present invention to provide a cannula having an adjustable length.

It is still another object of the present invention to provide a cannula whereby a vacuum can be connected to the cannula and whereby a common syringe can be used for introducing liquid into the inflatable seal.

These and other objects and advantages of the present invention will become apparent from a reading of the attached specification and appended claims.

BRIEF SUMMARY OF THE INVENTION

The present invention is a cannula having a tubular body with a proximal end and a distal end and a longitudinal channel extending therebetween. An inflatable ring is affixed within the tubular body adjacent the proximal end. The tubular body has a channel extending so as to be in fluid communication with the inflatable ring. A valve means is connected to the channel. This valve means is suitable for allowing a liquid to selectively pass into and from the inflatable ring. The inflatable ring is expandable into the longitudinal channel when the liquid is introduced thereinto.

In the preferred embodiment of the present invention, the tubular body has a first branch tube extending outwardly therefrom. A syringe has a portion received within the first branch tube. The syringe has a needle cooperative with the valve means so as to allow the syringe to introduce the liquid into the inflatable ring. The inflatable ring has a tubular port extending into this channel.

The tubular body has a threaded section adjacent the proximal end. A cap is threadedly engaged with this threaded section. The cap serves to retain the inflatable ring within the tubular body.

The tubular body has a second branch tube extending outwardly therefrom. The second branch tube has a valve cooperative therewith. The second branch tube is suitable for allowing a vacuum to be connected thereto. The second branch tube has a channel communicating with the longitudinal channel of the tubular body. Each of the first and second branch tubes extend outwardly on opposite sides of the tubular body and are spaced from the proximal end of the tubular body. Each of the first and second branch tubes has a curved gripping surface extending from an underside thereof toward the tubular body.

The tubular body has an outer sleeve extending toward the distal end. An inner sleeve is received within this outer sleeve. The inner sleeve has a distal end at an end opposite the outer sleeve. The inner sleeve is adjustably received within the outer sleeve such that the distal end can be set to a desired distance from the outer sleeve. The inner sleeve is threadedly connected to the outer sleeve. The inner sleeve has a plurality of indentations formed in an outer surface thereof. The plurality of indentations are evenly spaced from each other and longitudinally aligned. At least one of the indentations is releasably engageable with a complementary projection extending inwardly of the outer sleeve so as to fix a position of the inner sleeve with respect to the outer sleeve. The outer sleeve has a window formed through a wall thereof. The inner sleeve has numerical indicia formed thereon. The numerical indicia corresponds to a distance that the inner sleeve extends outwardly of the outer sleeve. At least one of the numerical indicia appear through the window when the complementary projections engage the indentation.

In the present invention, an instrument can extend through the longitudinal channel so as to extend outwardly of the proximal end and the distal end of the tubular body. The inflatable ring has an interior surface in generally liquid-tight abutment with a surface of the instrument when the inflatable ring is filled with the liquid. The instrument, in the preferred embodiment of the present invention, is a trocar that has a pointed end extending outwardly of the distal end and a handle positioned outwardly of the proximal end.

DETAILED DESCRIPTION OF THE INVENTION

Figure 1:
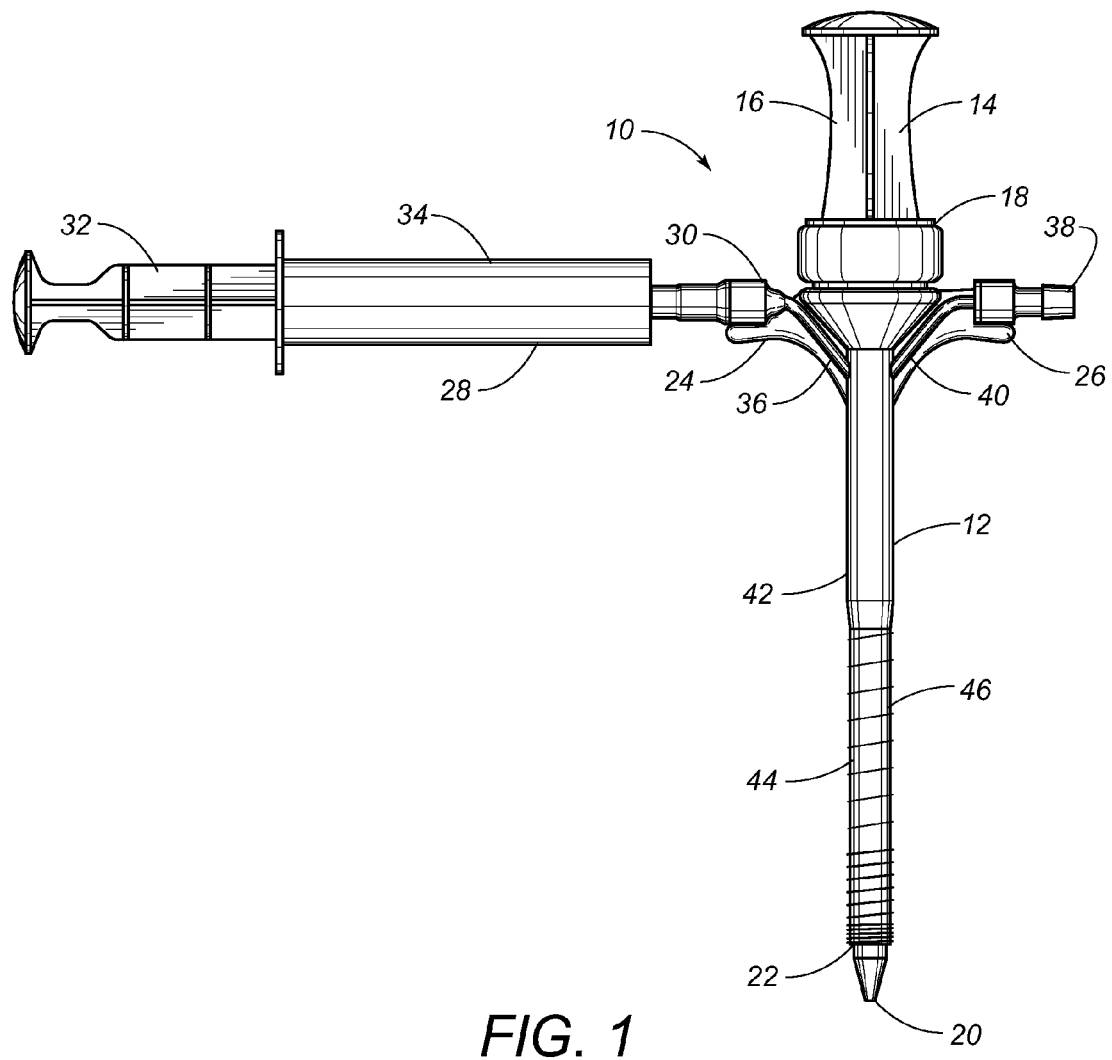
FIG. 1 is a side elevational view showing the cannula assembly in accordance with the preferred embodiment of the present invention.

Referring to FIG. 1, there is shown the cannula assembly 10 in accordance with preferred embodiment of the present invention. The cannula assembly 10 includes a tubular body 12 that has an inflatable ring (not shown) affixed therein. The tubular body is illustrated as receiving a trocar 14 therethrough. The trocar 14 has a handle 16 extending outwardly of a proximal end 18 of the tubular body and a pointed end 20 extending outwardly of a distal end 22 of the tubular body 12.

The tubular body 12 has a first branch tube 24 extending outwardly of one side of the tubular body and a second branch tube 26 extending outwardly of the other side of the tubular body. A syringe 28 is received within the first branch tube 24. Syringe 28 is configured so as to be able to deliver liquid to the inflatable ring within the tubular body 12 and also for the purposes of removing the liquid from the inflatable ring. In particular, a valve 30 is positioned within the first branch tube 24. Valve 30 is cooperative with the needle of the syringe 28 so as to allow liquid to be delivered to the inflatable ring. A piston 32 is received within the cylinder 34 of syringe 28. Piston 32 can be suitably pushed so as to deliver the liquid through a channel 36 and into the inflatable ring.

The second branch tube 26 also includes a suitable valve which allows a vacuum to be introduced into the port 38 and through a channel 40. The vacuum is connected by channel 40 to the interior passageway within the tubular body 12.

FIG. 1 particularly illustrates how the tubular body 12 includes an outer sleeve 42 and an inner sleeve 44. The inner sleeve 44 has threads 46 formed thereon. Threads 46 will engage complementary threads formed on the interior of the outer sleeve 42. A rotation of the inner sleeve 44 with respect to the outer sleeve 42 will allow the length of the tubular body 12 of the cannula assembly 10 to be suitably adjusted to the needs of the surgeon.

Figure 2:
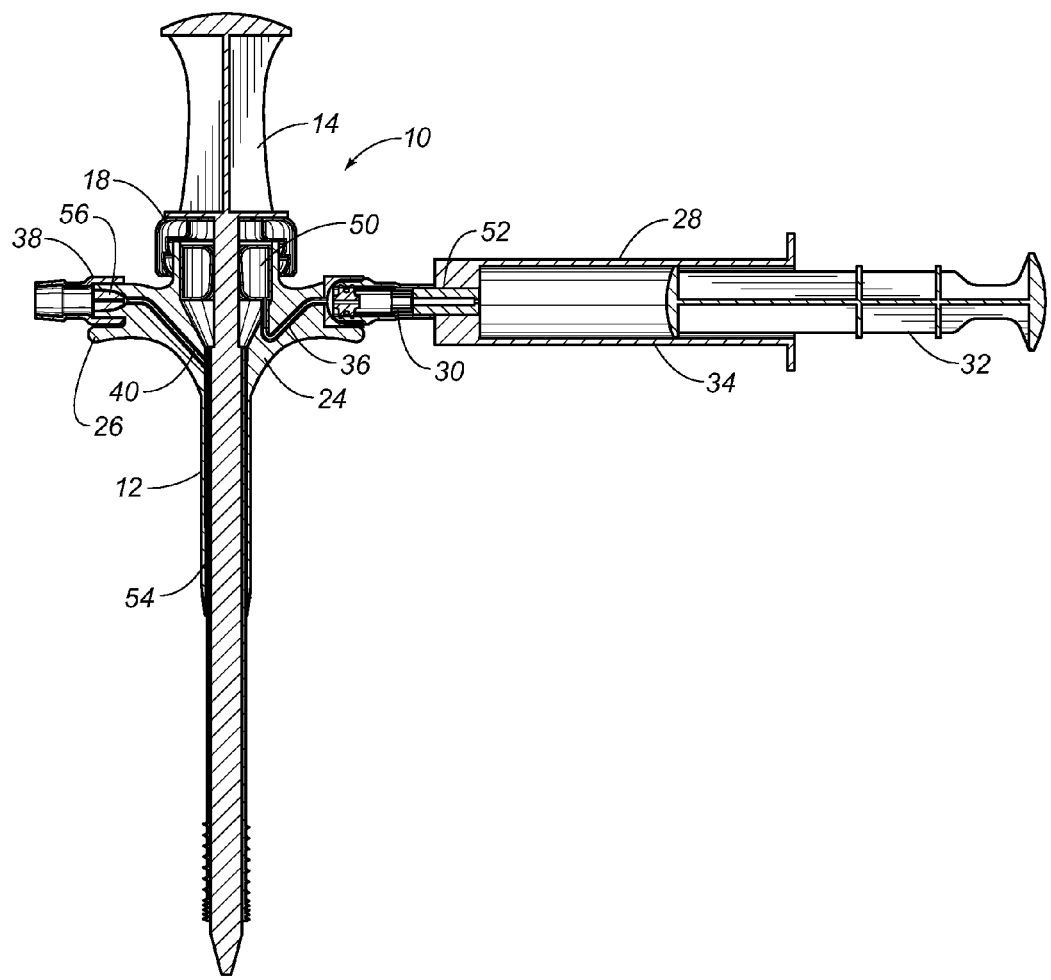
FIG. 2 is a cross-sectional view of the cannula assembly of the preferred embodiment of the present invention.

FIG. 2 shows a cross-sectional view of the cannula assembly 10 of the present invention. In FIG. 2, it can be seen that the inflatable ring 50 is affixed within the tubular body 12. Channel 36 extends through the branch tube 24 so as to communicate with the inflatable ring 50. As can be seen, the needle 52 of the syringe 28 extends through a valve 30 so as to communicate with the channel 36 and the inflatable ring 50. The piston 32 extends into the cylinder 34 of syringe 28 so as to allow liquid from the syringe 28 to be introduced into the inflatable ring. The instrument 14 (a trocar) extends through the interior passageway 54 of the tubular body 12. The inflatable ring 50 is illustrated as inflated so as to have an interior surface in generally liquid-tight abutment with the surface of the instrument 14. As such, the instrument 14 can be manipulated, as required, without having liquid from the body cavity passing outwardly of the proximal end 18 of the cannula assembly 10. Since the present invention utilizes a common hospital syringe 28 as the fluid-delivery mechanism, the present invention does not require specialized equipment for such introduction of liquid. Any common hospital syringe can work by simply introducing the needle of the syringe through the valve 30 and into the branch tube 24 associated with tubular body 12. Similarly, the second branch tube 26 has valve 56 positioned therein. A vacuum pump can be connected to port 38 so as to allow a vacuum to pass through the channel 40 and into the interior passageway 54. As such, the cannula assembly 10 of the present invention can also be used for introducing a vacuum into the body for the removal of fluids therein and for other purposes.

Figure 3:
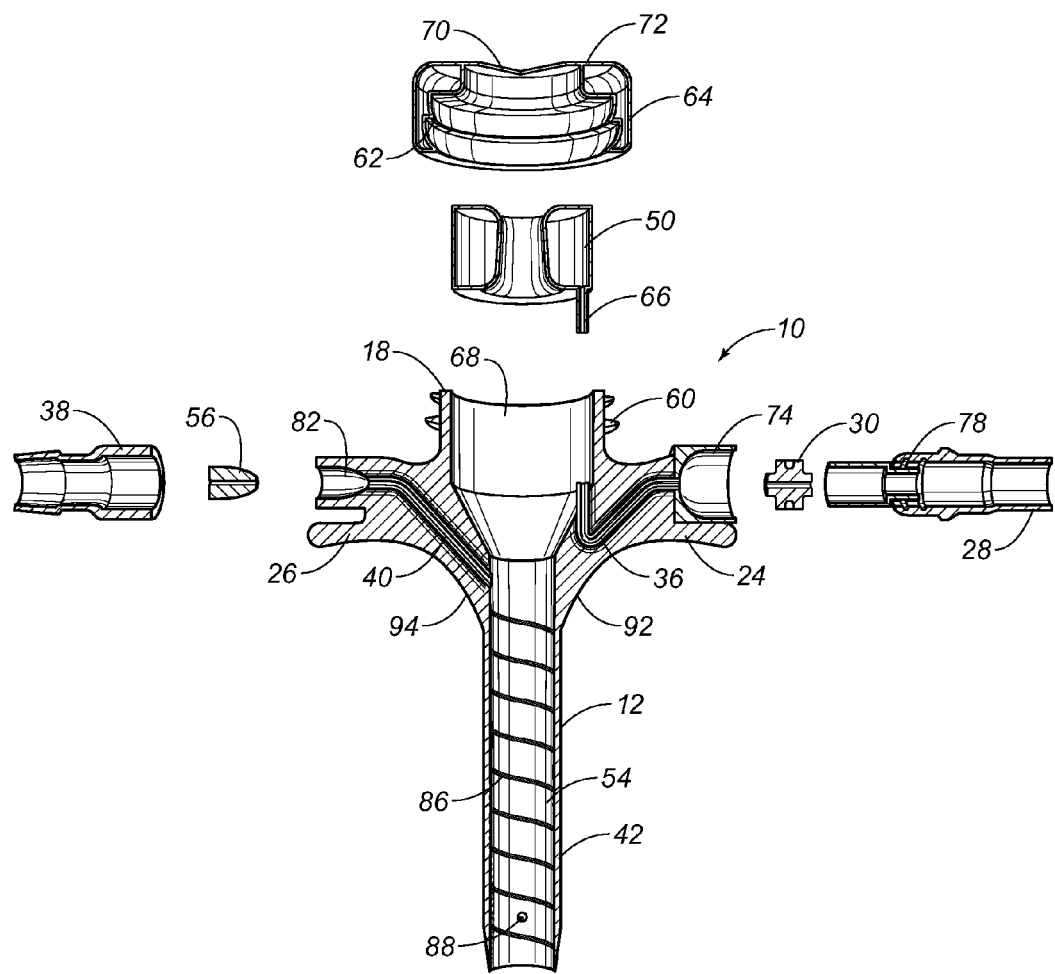
FIG. 3 is an exploded view of the cannula of the present invention.

FIG. 3 shows a detailed view of the components of the cannula assembly 10 of the present invention. Initially, it can be seen that the tubular body 12 has a threaded section 60 located at the proximal end 18 thereof. The threaded section 60 is in the form of exterior threads which are engageable with interior threads 62 associated with a cap 64. The inflatable ring 50 has a tubular port 66 extending downwardly therefrom. The tubular port 66 can be introduced into the channel 36 so as to be sealed within the channel 36 for allowing liquids to pass solely through the inlet of the tubular port 66. The inflatable ring 50 is fitted within an annular area 68 located at the proximal end 18 of the tubular body 12. When the inflatable ring 50 is installed into the annular area 68 of the tubular body 12, the cap 64 can have its interior threads 62 threadedly secured to the exterior threads 60 so as to secure the inflatable ring 50 within the tubular body 12. An opening 70 is formed in the top surface 72 of the cap 64 so as to allow the instrument 14 to be introduced into the tubular body 12 through the inflatable ring 50.

The first branch tube 24 has a receptacle 74 suitable for receiving valve 30 therein. Valve 30 is of a similar nature to that of a Foley™ catheter. The end 78 of the syringe 28 can be placed over and through the valve 30 so as to allow liquids to pass from the needle of the syringe 28 through the channel 36, through the tubular port 66, and into the interior of the inflatable ring 50.

The second branch tube 26 has channel 40 extending from inlet 82 to the interior passageway 54 of the tubular body 12. Another valve 56 is positioned within the receptacle 82 and within the port 38. A vacuum can be connected to the port 38 so as to remove liquids from the interior passageway 54.

The outer sleeve 42 of the tubular body 12 is particularly illustrated in FIG. 3. As can be seen, a threaded wall surface 86 is formed thereon. This threaded wall surface 86 is engageable with the threads 46 of the inner sleeve 44. A projection 88 is located near the end 90 of the outer sleeve 42. Projection 88 is engageable with a suitable indentation formed on the inner sleeve 44, as will be described hereinafter.

It should be noted that each of the branch tubes 24 and 26 includes respective curved gripping surfaces 92 and 94. These curved gripping surfaces extend from the underside of the respective branch tubes 24 and 26 toward the outer wall of the outer sleeve 42. These curved gripping surfaces 92 and 94 provide an area whereby the surgeon's fingers can be placed for the purpose of urging the instrument through the interior passageway 54 by pressure applied to the handle of the instrument above the proximal end 18 of the cannula assembly 10.

Figure 4:
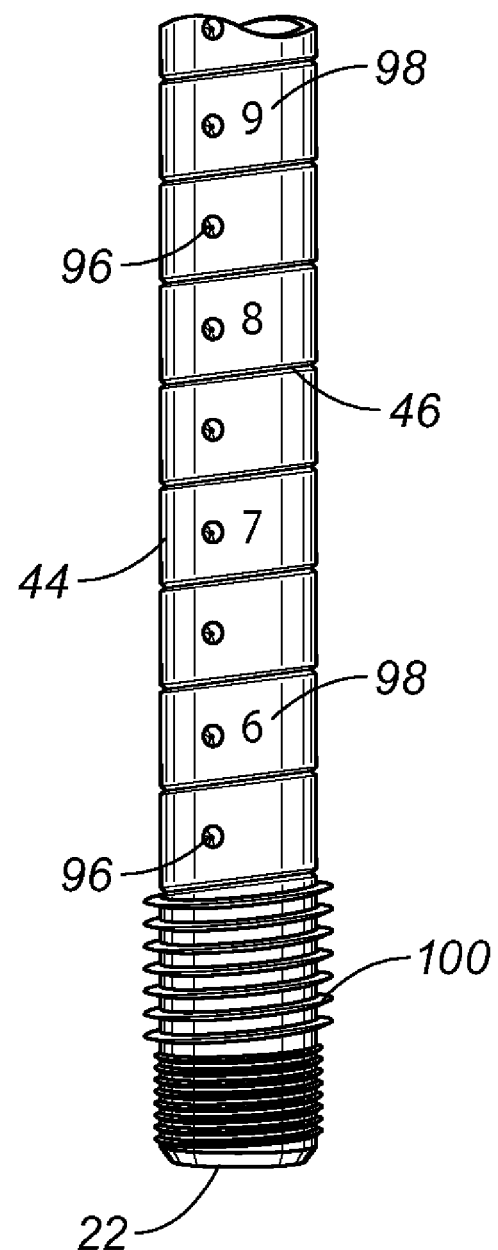
FIG. 4 is an isolated view of the inner sleeve, along with its associated numerical indicia, that is received within the outer sleeve of the tubular body of the cannula.

FIG. 4 shows a detailed view of the inner sleeve 44. It can be seen that the inner sleeve 44 includes threads 46 extending in a spiral pattern therearound. As illustrated in FIG. 4, the threads 46 are in the form of an indented surface formed into the wall of the inner sleeve 44. Alternatively, the threads 46 could project outwardly so as to engage internal threads formed on the outer sleeve 42. A plurality of indentations 96 are formed into the wall of the inner sleeve 44. Indentations 96 are evenly spaced from each other and longitudinally aligned along the inner sleeve 44. Numerical indicia 98 are associated with a particular indentation 96. Numerical indicia 98 are indicative of the distance that the distal end 22 of the tubular body 12 extends from the end of the outer sleeve 42 or into the human body. For example, when the projection 88 engages the indentation associated with the numerical indicia "8", then the surgeon will know that the distal end 22 is located approximately eight inches into the body. Threads 100 are formed adjacent to the distal end 22 in the nature of conventional cannula assemblies.

Figure 5:
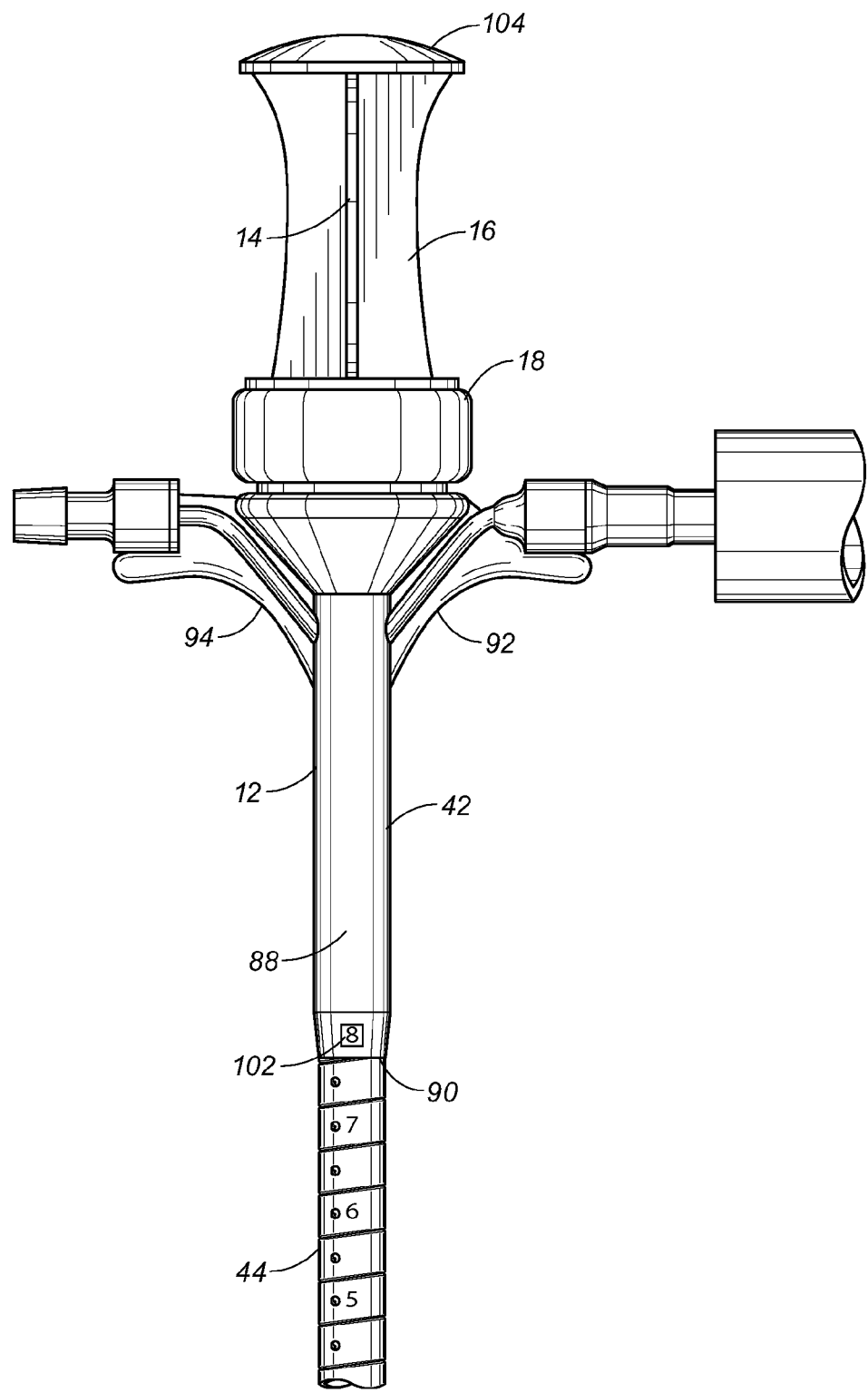
FIG. 5 is a detailed view showing how the numerical indicia appears through a window on the outer sleeve of the tubular body.

FIG. 5 illustrates a detailed view showing the relationship between the outer sleeve 42 and the inner sleeve 44. As can be seen, the numerical indicia "8" appears through a window 102 formed adjacent to the end 90 of the outer sleeve 42.

FIG. 5 also illustrates the manner in which the handle 16 of instrument 14 extends outwardly of the proximal end 18 of the tubular body 12. The curved gripping surfaces 92 and 94 are particularly illustrated in FIG. 5. In normal use, the surgeon may place his fingers on the gripping surfaces 92 and 94 and the palm of his hand upon the top 104 of the handle 16. As such, the strong force of the palm of the hand can be used so as to urge the instrument 14 through the interior passageway of the tubular body 12 and into the body.

In normal use, the pressing of the piston 32 of syringe 28 will deliver liquid into the inflatable ring. This will allow the inflatable ring 50 to have strong gripping forces in the area between the interior surface of the inflatable ring 50 and the exterior surface of the instrument 14. When the inflatable ring 50 is in its deflated configuration (caused by the pulling of the piston 32 from the cylinder 34), it is relatively easy to insert the instrument 14 through the interior passageway 54 of the tubular body 12. When the instrument 14 is in a desired position, the piston 32 can be depressed so as to fill the inflatable ring 50 with liquid until a strong sealing contact is established with the exterior surface of the instrument 14. This will allow the instrument 14 to be suitably manipulated because of the elastomeric material of the inflatable ring 50. The present invention provides liquid-tight sealing contact while, at the same time, allows full and complete manipulation of the instrument 14 in a desired manner. After the procedure has been completed, the surgeon can simply pull on the piston 32 so as to release liquid from the interior of the inflatable ring 50. The instrument 14 can then be simply pulled from the interior passageway in a conventional manner.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A cannula comprising:
a tubular body having a proximal end and a distal end with a longitudinal channel extending therebetween, said tubular body having a first branch tube extending outwardly therefrom, said tubular body having a second branch tube extending outwardly therefrom, said tubular body having a threaded section adjacent said proximal end;
an inflatable ring affixed within said tubular body adjacent said proximal end, said tubular body having a channel extending so as to be in fluid communication with said inflatable ring;
a first valving means connected to said channel, said first valving means for allowing a liquid to be selectively passed into and from said inflatable ring, said inflatable ring being expandable into said longitudinal channel when the liquid is introduced thereinto;
a second valving means cooperative with said second branch tube, said second valving means for allowing a vacuum to be passed through said second branch tube and into said longitudinal channel of said tubular body; and
a cap threadedly engaged with said threaded section, said cap retaining said inflatable ring within said tubular body.

2. The cannula of claim 1, further comprising:
a syringe having a portion received within said first branch tube, said syringe being cooperative with said first valving means so as to allow said syringe to introduce the liquid into said inflatable ring.

3. The cannula of claim 1, said inflatable ring having a tubular port extending into said channel.

4. The cannula of claim 1, each of said first and second branch tubes extending outwardly from opposite sides of said tubular body and spaced from said proximal end of said tubular body.

5. The cannula of claim 4, each of said first and second branch tubes having a curved gripping surface extending from an underside thereof toward said tubular body.

6. A cannula comprising:
a tubular body having a proximal end and a distal end with a longitudinal channel extending therebetween, said tubular body having an inner sleeve adjustably received within an outer sleeve, said inner sleeve having said distal end at an end opposite said outer sleeve, said inner sleeve having a plurality of indentations formed in an outer surface thereof, said plurality of indentations being evenly spaced from each other and longitudinally aligned, at least one of said plurality of indentations being releasably enagageable with a complementary projection extending radially inwardly of said outer sleeve so as to fix a position of said inner sleeve with respect to said outer sleeve;
an inflatable ring affixed within said tubular body adjacent said proximal end, said tubular body having a channel extending so as to be in fluid communication with said inflatable ring; and
a valving means connected to said channel, said valving means for allowing a liquid to be selectively passed into and from said inflatable ring, said inflatable ring being expandable into said longitudinal channel when the liquid is introduced thereinto, said outer sleeve having a window formed through a wall thereof, said inner sleeve having numerical indicia thereon, said numerical indicia corresponding to a distance that said inner sleeve extends outwardly of said outer sleeve, at least one of said numerical indicia appearing through said window when said complementary projection engages the indentation.

7. The cannula of claim 6, said inner sleeve being threadedly connected to said outer sleeve.

8. The cannula of claim 6, further comprising:
an instrument extending through said longitudinal channel so as to extend outwardly of said proximal and said distal end, said inflatable ring having an interior surface in generally liquid-tight abutment with a surface of said instrument when said inflatable ring is filled with the liquid.

9. The cannula of claim 8, said instrument being a trocar having a pointed end extending outwardly of said distal end and a handle positioned outwardly of said proximal end.

10. A cannula comprising:
a tubular body having a proximal end and a distal end with a longitudinal channel extending therebetween, said tubular body having an outer sleeve extending toward said distal end, said tubular body having an inner sleeve received within said outer sleeve, said inner sleeve having said distal end at an end opposite said outer sleeve, said inner sleeve being adjustably received within said outer sleeve such that said distal end can be set to a desired distance from said outer sleeve, said inner sleeve having a plurality of indentations formed in an outer surface thereof, said plurality of indentations being evenly spaced from each other and longitudinally aligned, at least one of said plurality of indentations being releasably engageable with a complementary projection extending inwardly of said outer sleeve so as to fix of said inner sleeve with respect to said outer sleeve, said outer sleeve having a window formed through a wall thereof, said inner sleeve having numerical indicia thereon, said numerical indicia corresponding to a distance that said inner sleeve extends outwardly of said outer sleeve, at least one of said numerical indicia appearing through said window when said complementary projection engages the indentation.

11. The cannula of claim 10, further comprising:
an inflatable ring affixed within said tubular body adjacent said proximal end, said tubular body having a channel extending so as to in fluid communication with said inflatable ring; and
a valving means connected to said channel, said valving means for allowing a liquid to be selectively passed into and from said inflatable ring, said inflatable ring expandable into said longitudinal channel when the liquid is introduced thereinto.

* * * * *